(12) United States Patent
Hill et al.

(10) Patent No.: US 9,040,236 B2
(45) Date of Patent: May 26, 2015

(54) BIOLOGICAL FLUID SAMPLING AND STORAGE APPARATUS FOR REMOTE USE

(75) Inventors: Jeanette Hill, Manor, TX (US); James Hill, Manor, TX (US)

(73) Assignee: Spot on Sciences, Inc., Austin, TX (US)

( * ) Notice: Subject to any disclaimer, the term of this patent is extended or adjusted under 35 U.S.C. 154(b) by 0 days.

(21) Appl. No.: 13/817,442

(22) PCT Filed: Jul. 25, 2011

(86) PCT No.: PCT/US2011/045167
§ 371 (c)(1),
(2), (4) Date: Feb. 16, 2013

(87) PCT Pub. No.: WO2012/027048
PCT Pub. Date: Mar. 1, 2012

(65) Prior Publication Data
US 2013/0143226 A1   Jun. 6, 2013

Related U.S. Application Data

(60) Provisional application No. 61/377,323, filed on Aug. 26, 2010.

(51) Int. Cl.
*G01N 1/10* (2006.01)
*A61B 5/151* (2006.01)
*A61B 10/00* (2006.01)

(52) U.S. Cl.
CPC .............. *G01N 1/10* (2013.01); *A61B 5/15142* (2013.01); *A61B 5/15144* (2013.01); *A61B 10/0045* (2013.01); *A61B 10/0051* (2013.01); *A61B 10/007* (2013.01); *A61B 10/0096* (2013.01); *A61B 2010/0067* (2013.01); *A61B 2010/0077* (2013.01); *A61B 5/15101* (2013.01)

(58) Field of Classification Search
None
See application file for complete search history.

(56) References Cited

U.S. PATENT DOCUMENTS

| | | | |
|---|---|---|---|
| 6,036,659 A * | 3/2000 | Ray et al. ...................... | 600/573 |
| 2004/0161788 A1 | 8/2004 | Chen et al. | |
| 2005/0130310 A1 | 6/2005 | Wandell et al. | |
| 2007/0173741 A1* | 7/2007 | Deshmukh et al. ........... | 600/583 |
| 2008/0220461 A1 | 9/2008 | Kuriger | |
| 2009/0247902 A1 | 10/2009 | Reichert et al. | |
| 2010/0174211 A1 | 7/2010 | Frey et al. | |
| 2011/0077554 A1* | 3/2011 | Roe et al. ...................... | 600/583 |

* cited by examiner

*Primary Examiner* — Betty Forman
(74) *Attorney, Agent, or Firm* — Winstead PC

(57) ABSTRACT

An apparatus for sampling and storing biological fluids from a human or animal subject is provided. In one embodiment of the present disclosure, the apparatus includes a main body, lancet carrier or hub, lancet, lancet trigger, capillary tube, and sample compartments for collecting and storing dried blood and other bodily fluids. The lancet hub supports a lancet and provides for moving the lancet longitudinally between a first retracted position and a second extended position. The device includes a capillary tube having an internal diameter sized to draw and retain fluid from a contacted source using capillary action. The main body of the apparatus further includes a sample compartment for holding sampling and storage materials. In at least one embodiment of the present disclosure, the sample compartment can be accessed by lifting sample compartment lid. Also included is a new "fan" or "daisy" shaped collection material format for use in collecting and preserving samples.

17 Claims, 10 Drawing Sheets

BIOLOGICAL FLUID SAMPLING AND STORAGE APPARATUS FOR REMOTE USE

FIELD OF THE INVENTION

The present invention generally relates to the collection and storage of blood and other biological fluids for subsequent testing. More particularly, the present invention is concerned with a method and apparatus for a single use collection of a body fluid and storage of a dried sample.

BACKGROUND

The current, most widely used procedure for diagnostic blood sample collection is venipuncture. This method generally requires a trained phlebotomist and sterile equipment including needles/lancets and collection tubes. The blood samples collected by venipuncture usually require separation by centrifugation and storage under refrigeration. An alternate method uses a lancet for skin piercing such as a finger stick. For example, U.S. Pat. No. 4,920,977 describes a blood collection assembly with lancet and microcollection tube, while U.S. Pat. No. 5,368,047, No. 4,654,513, and No. 5,320,607 each describe suction-type blood samplers. These devices develop suction between the lancing site and the end of the device when the lancet holding mechanism withdraws after piercing the skin. A flexible gasket around the end of the device helps seal the end around the puncture site until adequate sample is drawn from the puncture site or the user pulls back on the device. Finally, U.S. Pat. No. 4,637,403 and Douglas et. al. WO1997042882 disclose combination lancing and blood collection devices which uses a capillary passage to conduct body fluid to a separate test strip in the form of a microporous membrane. With the U.S. Pat. No. 4,637,403 device, it is necessary to achieve a precise positioning of the upper end of the capillary passage with respect to the membrane in order to ensure that body fluid from the passage is transferred to the membrane. If an appreciable gap exists between the two, no transfer may occur—thus careful training and use is needed to properly obtain specimens with this device. The WO1997042882 device solves this problem by affixing a test strip to the capillary tube. Despite these advances in the art of blood collection, they all suffer from the drawback of obtaining liquid samples which must either be tested immediately, or require refrigeration to store and test later, and in any case require extensive use of sterile lab equipment to handle properly.

An alternative method known as dried blood spot (DBS) sampling has also been used for screening newborns for congenital metabolic diseases. In this sampling technique, an infant's heel is pricked by a trained health aide and the blood is spotted on a prepared filter paper. Typically, the spotted filter paper with the blood sample is air dried for several hours before being shipped at ambient temperature to a central state health lab. The blood spot is sampled by a hole punch (3-6 mm diameter), and the punched sample is placed in a tube and eluted with buffer. The extracted sample then undergoes multiple diagnostic tests; a quarter size blood spot sample is sufficient for at least 28 separate tests.

Although DBS has been used for newborn screening, DBS has not been used for routine diagnostic testing. Despite this, numerous studies have shown that DBS sampling is compatible with and equivalent to current diagnostic tests performed with fresh blood samples. Once dried, analytes including DNA, RNA, proteins and small molecules are stable at ambient temperature or under refrigeration for years (De Jesus et al., Clin Chem, 55 (1); 158-164, 2009; McDade, Demography 44(4): 899-925, 2007; Khoo; Pathology International; 61: 1-6, 2011). Analytes are simply extracted from the paper with solvent and measured by traditional methods including LC-MS/MS, RT-PCR, microarray, ELISA, etc. (McDade, Demography 44(4): 899-925, 2007; Haak, Neonatology 95(3), 210-216, 2009). Genetic material can be extracted and isolated from DBS in sufficient quantities for use in genetic analysis. For instance, DBS has been used for the detection of prenatal human immunodeficiency virus (HIV) infection by the polymerase chain reaction (PCR) (Cassol, et al., J. Clin Microbiol. 30 (12): 3039-42, 1992). Dried plasma spot (DPS) and DBS have also been used for HIV RNA detection and quantification (Cassol, et al., J. Clin. Microbiol. 35: 2795-2801, 1997; Fiscus, et al., J. Clin. Microbiol. 36: 258-60, 1998; O'Shea, et al., AIDS 13: 630-1, 1999; Biggar, et al., J. Infec. Dis. 180 1838-43, 1999; Brambilla, et al., J. Clin. Microbiol. 41(5): 1888 93, 2003); HIV DNA detection and quantification (Panteleefe, et al., J. Clin. Microbiol. 37: 350-3, 1999; Nyambi, et al., J. Clin. Microbiol. 32: 2858-60, 1994); and HIV antibody detection (Evengard, et al., AIDS 3: 591-5, 1989; Gwinn, et al., JAMA 265: 1704-08, 1991). HCV RNA detection and genotyping are also reported using DBS (Solmone et al., J. Clin. Microbio. 40 (9): 3512-14, 2002.

However, currently available DBS methods show decreased stability of dried samples when exposed to humidity. Inconsistent application of blood to the filter paper can also result in variable test results. Exposure of the filter paper to air and surfaces during drying or shipment can result in sample contamination. For example, U.S. Pat. No. 6,534,533 provides for a a device to collect and dry blood samples for testing, however, the invention dries the blood using evaporation into the environment, and in various embodiments of the invention, the dried blood spot is exposed to the environment, either directly or through a vapor or fluid permeable membrane. This means that environmental moisture can re-enter the device, potentially damaging or contaminating the sample. Further, separate components, such as a lancet, filter papers, a holder for drying and containers with drying agent for transport are needed for sampling with current DBS methods. These separate components can be cumbersome for use by a skilled technician and are not suitable for use by the patient alone. Furthermore, this method requires disposal of collection materials as hazardous waste.

Consequently, a need exists for improvement in sampling and storage techniques to collect minimal blood amounts in remote locations with minimal training required, no additional infrastructure needs, to ease transport requirements and to improve sample stability.

Additionally, predictable and even distribution of a sample within a sampling material is difficult to obtain with current techniques. Currently, biological sample distribution across the collection material is dependent on sample application technique and can result in uneven analyte concentration across the material. Variable analytical results can occur when a sub-sample within the diameter of the sample spot is removed manually with a hole punch, which is the current and time-consuming method for sample removal. Therefore, there is a need for an apparatus or method that increases the evenness and predictability of sample distribution on collection materials while maintaining or enhancing ease of sample preparation.

The present invention seeks to provide for an all-in-one body fluid collection and storage device as a dried sample providing for increased sample stability/longevity and protection from contamination or degradation.

The present invention further seeks to provide for an all-in-one body fluid collection and storage device containing all of the components necessary to obtain and store the dried sample, increasing ease of use and reducing reliance on outside equipment.

Additionally, the present invention seeks to provide a configuration of collection materials that allows for consistent biological sample distribution and efficient removal of a sub-sample for analysis.

SUMMARY OF THE INVENTION

The present disclosure provides in certain embodiments, a single-use apparatus for body fluid sample collection and storage as a dried sample comprising structural components that form an interior chamber(s) containing a sample collection material(s) and a desiccant, the sample collection material being in fluid communication with a capillary tube or opening that extend to the exterior of the device and through which the user introduces the fluid to be collected. The device also optimally includes a detachable lancing mechanism for puncturing the skin. The disclosed devices can be operated with minimal training requirements in remote locations with no additional infrastructure requirements, and provides ease of transport and sample stability at ambient temperature and humidity. The invention of the present disclosure provides for:

a. Simplified collection technique. With the all-in-one device, if the sample to be collected is blood, the sampling site is pricked by a lancet integrated with the cartridge. Blood drops are drawn into the cartridge by capillary action to the absorbent material. Other body fluids can be collected without pricking the skin, simply by placing the fluid onto the capillary tube. This ease of use and handling allows for self sampling by patient in a remote location with no external reagent, equipment or infrastructure requirements.

b. Protection from contamination and ambient humidity. The enclosed cartridge includes a drying agent in vaporous communication with the sampling material. Once the sample is drawn into the cartridge, it spreads out evenly on the filter paper where it is dried rapidly by the desiccant. The DBS sample is then protected from contamination or ambient humidity and is ready for transport and/or storage, eliminating the need for time-consuming air-drying. This significantly improves convenience for remote sampling.

c. Consistent sample distribution and simplified removal for elution. Blood drops will be conveyed to the center of the absorbent material which is preferably pre-cut in a configuration to aid even distribution of the sample. Each wedge contains equal amounts of sample and are easily removed for analysis. This is in contrast to current DBS methods that require a time-consuming manual hole punch for sample removal and potential distortion of results due to uneven analyte distribution across the diameter of the disc.

d. Improved sample tracking Customizable bar codes or other identification mechanisms found on the exterior of each cartridge provide accurate identification of each sample. Removable bar code stickers on or packaged with each cartridge allow for simplified labeling of downstream testing materials such as elution tubes.

e. Integrated desiccation for long-term storage and future testing. Once individual portions of the filter disc are removed for elution, the remaining sample segments can remain enclosed within the cartridge with its own desiccant and stored for long periods at ambient or refrigeration temperatures. A secure, tamper-evident latch allows for easy opening and closing to remove sample portions for further testing.

The all-in-one design of the device makes it ideally suited for collection of DBS samples in the field, where conventional DBS or venipuncture sample collection would be difficult.

Accordingly, the present disclosure relates to an apparatus for collecting and storing biological fluid, which comprises: a single body container comprising all elements needed for sample collection and storage including a lancet for pricking skin, a capillary tube or small opening for transporting fluid, a solid support such as pre-cut absorbent material for holding the fluid, a drying agent to rapidly dry the sample in a container with open and close access for samples.

The invention also includes a new configuration for collection materials for use within the invention and in other sampling applications comprising one or more sheets of such material comprising a small central disk from which radiate a number of identical protrusions separated by a number of empty spaces (which may be imagined similar to a daisy with petals) such that a sample is contacted with the central disk and is absorbed into the protrusions. The empty spaces between the protrusions allow for increased drying speed and contact with a support structure for stability. The protrusions are so designed as to be easily separable from the central disk, so that each petal may be detached and tested—since each petal has a uniform area and thickness, the amount of sample absorbed on each should be identical.

DETAILED DESCRIPTION OF THE PREFERRED EMBODIMENTS OF THE INVENTION

Figure 1A:
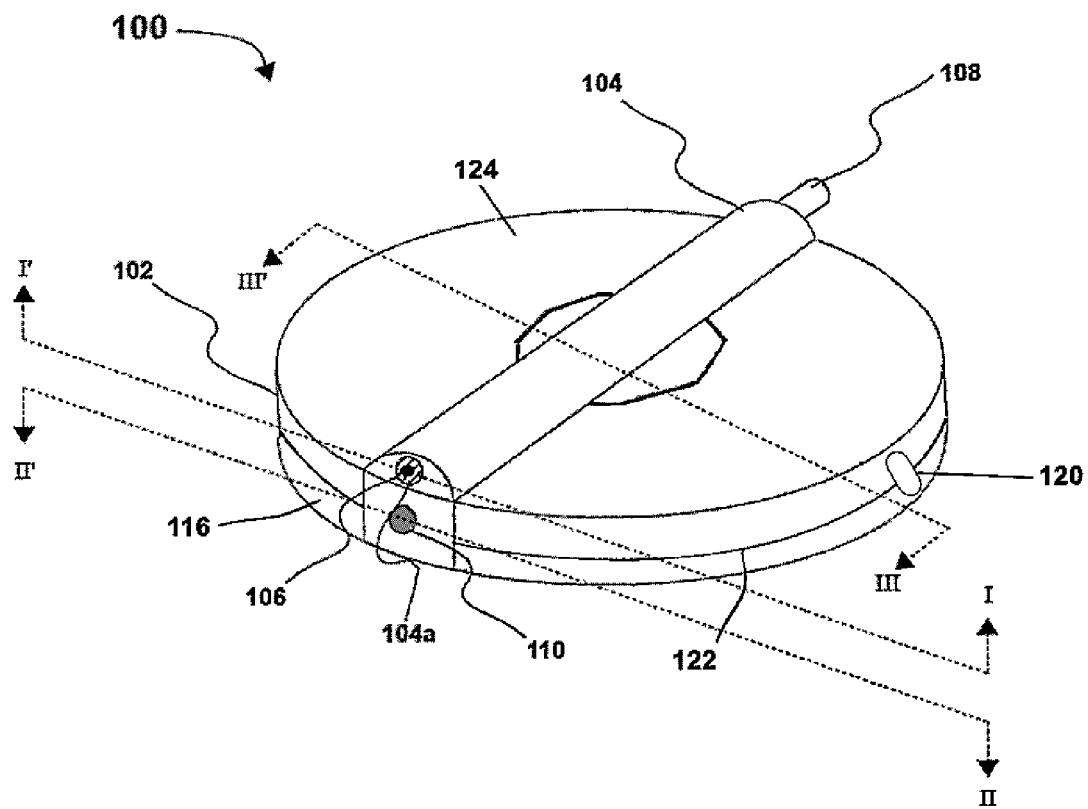
FIG. 1A illustrates an exemplary embodiment of the apparatus of the present disclosure packaged prior to use.

As used herein, the term "capillary tube" refers to one or more narrow tubes of any length that moves a fluid at least partially through capillary action. The interior diameter of a tube is generally between about 0.5 and 5 mm in diameter, but may be larger or smaller depending on the nature of the sample to be collected, the physical composition of the tube, and any coating placed on the tube. The tube may also vary in diameter along its length, as by, for example, being wider or narrower at the "top" or "bottom." One skilled in the art would be able to chose an optimal diameter and length for fluid transport with minimal experimentation. It is important to note herein that fluid may move through a "capillary tube" via other mechanisms as well, such as by gravity or by pressure differential, and that these mechanisms may be responsible for more motivational force than the capillary action within the capillary tube alone. It is intended that such tubes be included within our definition of "capillary tube" as used herein.

In a broad sense, the invention of the current disclosure may be envisioned as a body fluid sampling device that comprises at least two structural components that can be reversibly attached to one another in such a manner as to form at least one largely sealed central chamber when the components are in the "closed" or "fully attached" positions. These structural components may be made of any suitable material for collecting body fluids, such as glass, plastic, or stainless steel, among others. This reversible attachment may be accomplished by a variety of known mechanisms, such as by screwing the components together, attaching the top(s) and bottom(s) with a hinge(s) and clasp(s), by pressing the structural components together such that friction holds the components together, or by having one component slide into another component in a manner like a drawer. Other mechanisms of attaching the structural components will be readily apparent to one skilled in the art. In addition, the central chamber formed by the structural components is connected to the outside environment by a capillary tube or opening, such that fluid from the outside of the device is drawn into the central chamber(s) via capillary action. This tube may be an integral part of a structural component, or may be an additional component inserted through one or more of the structural components. The interior diameter of the capillary tube(s) according to this invention will necessarily vary based on at least: 1) the nature of the fluid to be collected, 2) the material(s) that the capillary tubes are made of, and 3) any special coating placed on the interior of the tube. In some embodiments of the invention, the structural component(s) bearing the capillary tube(s) may be replaced after sample collection by a similar tube-less component to provide a sealed chamber for long term storage. More information on the particulars of the structural components is found in the descriptions of the figures, below.

In some preferred embodiments of the invention, there is provided a mechanism for sealing the sample collecting opening or capillary tube of the structural component(s) above, so as to ensure sterility and immunity to environmental influences such as moisture. The sealing mechanism may be anything which one skilled in the mechanical art would recognize, such as: a sticker placed over the outside opening of the capillary tube, a plug placed within the capillary tube, a movable door or slide that can be positioned to cover the capillary opening, pinching or twisting the capillary tube so that it is sealed, and replacing the capillary tube containing structural component with a structural component not containing a capillary tube, amongst others.

In some preferred embodiments of the invention, the interior chamber(s) contains one or more sampling material suitable for collecting the body fluid. Such sample collecting materials can include, as non limiting examples, filter paper or other solid support made from materials including nylon, polypropylene, polyester, rayon, cellulose, cellulose acetate, mixed cellulose ester, glass microfiber filters, cotton, quartz microfiber, polytetrafluoroethylene, polyvinylidene fluoride and the like. In some preferred embodiments of the invention, the sample collecting materials can be chemically treated to assist sample retention, test preparation, or increase sample longevity, amongst other things. Non-limiting examples include: to inactivate bacteria and/or viruses; to denature proteins; to lyse cells, to inactivate proteases, RNAses, DNAses and other enzymes, and/or to aid in sample preparation. In some preferred embodiments, the sampling material may be perforated or partitioned so as to provide the sampler or tester with readily separable pieces of sampling material. In other particularly preferred embodiments, the sample collecting materials are in fluid communication with the capillary tube(s). In some embodiments of the invention, the sampling material(s) are supported by a physical support structure. In some embodiments of the invention, the support structure may be a part of either the top or bottom structural components. In other embodiments of the invention, the support structure is a separate removable part or parts. More information on the particulars of the sampling components is provided when describing the figures below.

In some preferred embodiments of the invention, the collection material will be formed into a configuration with a center area for application of the liquid sample and surrounding protrusions or "petals" to receive the sample evenly by wicking or absorbing action. A sub-sample for analysis may be removed by plucking a petal from the collection material.

In some preferred embodiments of the invention, the interior chamber(s) contain a drying agent or desiccant to remove moisture from the sample. One skilled in the art will realize that the type of drying agent used, and the volume used, and the spatial placement within the device will depend on the body fluid used. More information on the drying components is provided when describing the figures, below.

In some preferred embodiments of the present invention, the device additionally comprises a lancet, needle, or other mechanism to puncture the skin in order to provide access to the particular body fluid (Hereinafter, "lancet" will be used to refer to all such puncturing mechanisms, for simplicity). In particularly preferred embodiments, the lancet is attached to the device, and located so that the lancet or tip is present at, or can be made present at, a location close to the outer entrance to the capillary tube. In particularly preferred embodiments, the lancet is part of a retractable "sticking" mechanism that the user operates, such that the lancet is ordinarily safely stored within the mechanism, and only emerges to prick the skin when the operator desires. One skilled in the art will recognize that there are a variety of retractable lancet sticking mechanisms suitable for use in this invention. In some embodiments of the invention, the lancet mechanism will be reversibly, non-permanently attached, for example, as by a peg or pegs, one or more dovetail-slides, latches, or by some other durable but reversible means of attachment. Details of the lancet mechanism will be discussed more fully below in the description of the figures.

The attached drawings and figures represent examples of some particularly preferred embodiments of the invention. One skilled in the art will recognize that there are alternative arrangements and compositions of the components described in the drawing that still fall within the spirit of the invention.

Referring now to the drawings, and more particularly, to FIG. 1A, there is shown a single-step blood and biological fluid sampling and storage apparatus, generally designated 100. Apparatus 100 includes a main body 102, which includes a housing including a top portion 124 and a bottom portion 116, which are connected by a hinge area 120 such that the device can be opened by separating the top portion and bottom portion along line 122. The device further includes a clasp, not shown, on the opposing side from the hinge to secure the device in a closed position. A lancet carrier or hub 104, is disposed on the top surface of the top portion and extends from one edge to the opposing edge. The hub 104 provides a channel for a capillary tube 110, and a lancet device 106, which includes a lancet trigger 108. The lancet device is shown in the retracted state. The trigger 108 can be pressed to release the lancet such that the sharp tip is forcefully extended beyond the housing 104a to penetrate an area of tissue or skin held next to the housing. Main body 102 further provides a housing for the capillary 110, which has an internal diameter sized according to its composition, coatings (if any), to draw and retain the specific fluid from a contacted liquid source using capillary action. Main body 102 further includes a sample compartment for holding an absorbent material for collection, storage and shipping of body fluid samples.

The apparatus is sized to be easy to use with only one hand so that it is amenable to self collection of fluid samples. The device or apparatus can be from about 3 to 6 cm in diameter, or in certain embodiments from about 4 to 5 cm in diameter with a height of about ½ to 1 cm or more including the hub. The size can be changed to accommodate different uses or different users without departing from the spirit of the disclosure. The apparatus or device housing can be composed of any suitable lightweight and inexpensive materials such as polypropylene, polystyrene, glass or other suitable materials. The housing can be transparent such that sample filling can be observed. The housing optionally contains a unique identifier such as a bar code, numbers or letters so that it can be linked to a specific sample collection and subject. The shape of the apparatus can be a circle, oval, square, polygon or rectangle, or other such easily graspable shape. In one embodiment of the present disclosure, the sample compartment can be accessed by separating the top and bottom along the hinged area 120 thus exposing the sample compartment. In another embodiment of the present disclosure, the sample compartment can be accessed by means of a sliding drawer. In another embodiment of the present invention, the sample compartment may be accessed by unscrewing the top portion from the bottom portion.

Figure 1B:
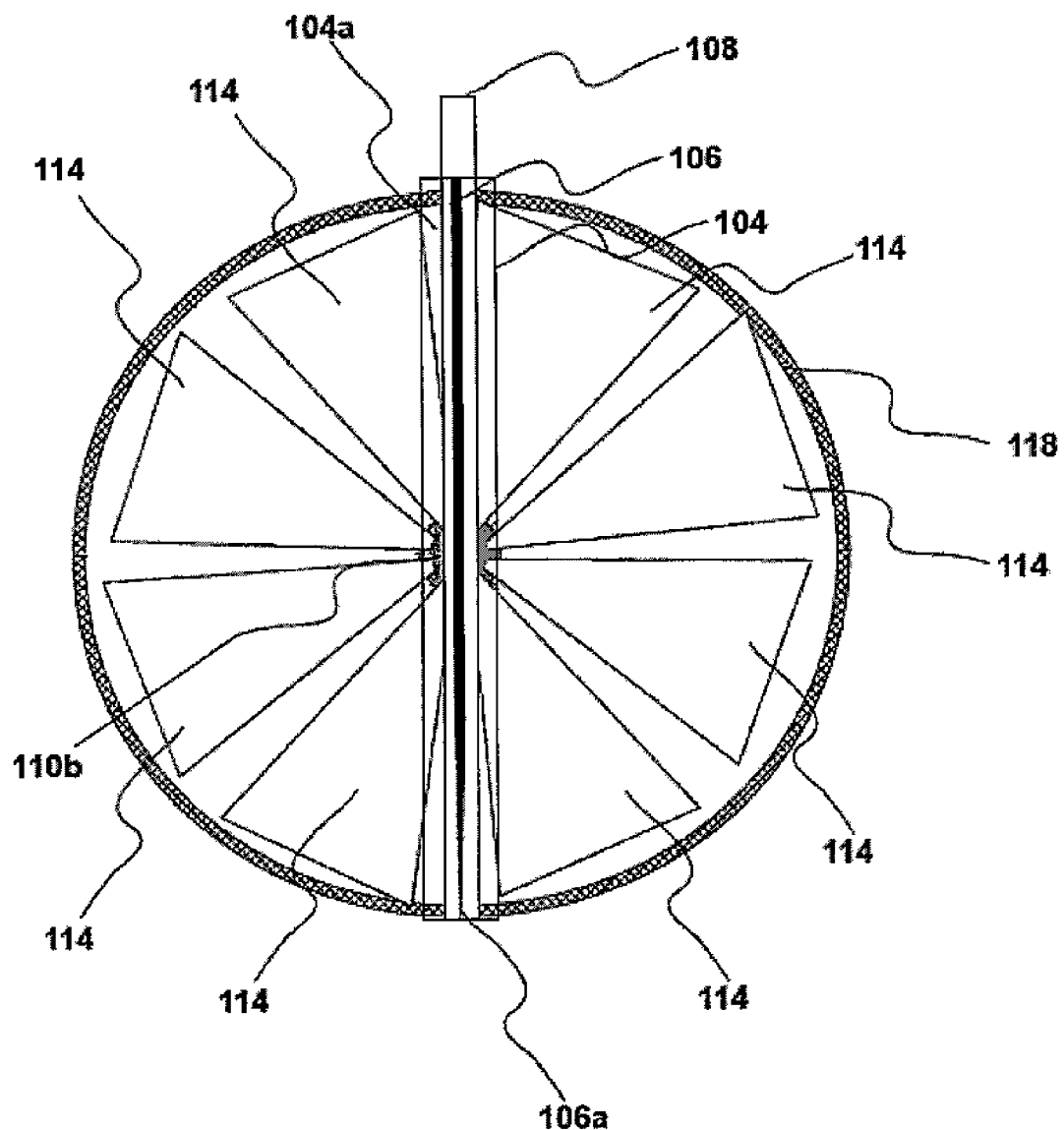
FIG. 1B illustrates a top sectional view of an embodiment of the apparatus of the present disclosure.

Referring now to FIG. 1B there is shown a top cross-sectional view of an apparatus embodying the invention. 100 taken about line I-I of FIG. 1A. FIG. 1B illustrates lancet hub 104 disposed diametrically along main body 102. Lancet hub 104 includes a housing 104a for receiving a lancing element or lancet 106. Lancing element or lancet 106 is received in housing 104a and longitudinally movable within housing 104a of apparatus 100 between a first, retracted position, and a second, extended position. Means are provided for resiliently extending and retracting the lancet in order to make a desired incision and to then withdraw the lancet back into a shielded position.

Optionally, the top component may be removable and replace with a separate top component having no openings to allow for long term storage.

Various means for extending a lancet relative to a housing are known in the art, and are useful in combination with the present disclosure (such as that of the patent application of Karbowniczek, Ser. No. 11/123,849). In one embodiment of the present disclosure, lancet 106 is held by carriers that are spring loaded for movement relative to the surrounding housing 104a. In another embodiment of the present disclosure, a spring-loaded hammer can be used to impact lancet 106 in order to drive it in the direction to lance the skin. Such means known in the art typically extend the lancet to a defined extent, such as by moving the lancet to a stop. Such devices frequently are produced with a predefined limit of travel for the lancet, thereby defining a penetration for the lancet into the skin. Alternatively, devices are well known which permit the user to adjust the penetration depth, such as by turning a wheel or other mechanism, with such adjustable devices frequently including a dial or other display which indicates the selected depth. These types of mechanisms are useful in as lancet mechanisms according to the present invention.

Various means can similarly be employed for retracting the lancet after it has made the incision, and many such mechanisms are known in the art. In one embodiment of the present disclosure, a refraction means is a spring surrounding lancet 106 and disposed between bearing surfaces or retainers associated with main body and bearing surfaces or retainers associated with lancet 106. Exemplary bearing surfaces can be selected from a group comprising fingers, tabs, flanges, rings, or similar structures which provide sufficient bearing surfaces to retain a spring in place without materially impeding longitudinal movement of lancet 106.

Withdrawal of lancet 106 can also be either a full or a partial withdrawal. When fully withdrawn, lancet 106 is removed from the incision and returned to the retracted position protected from accidental contact by the user. In an alternate approach, lancet 106 could be partially withdrawn, thereby leaving a portion of the lancet remaining within the incision. When lancet 106 is only partially withdrawn, lancet 106 acts as a focal point for locating body fluid and transferring it to capillary tube 110. This can be useful to ensure that the incision remains open for the body fluid to flow out of the incision.

Main body 102 further includes a capillary tube 110 located adjacent to cavity 104a and extending from the cavity to the outside surface, for drawing and retaining fluid from a contacted source using capillary action. Capillary tube 110 performs a capillary function in that body fluid is drawn up through apparatus 100 within capillary space 110a, with displaced air escaping from the unit through the opposing end of body 102. Capillary tube 110 is sized and arranged to provide the desired flow of biological fluid through capillary action. The interior diameter is determined by the fluid to be moved, the material the capillary tube is made out of, and any coatings within the capillary tube. One of ordinary skill would be able to size the capillary tube's interior diameter according to the above factors without undue experimentation. In one embodiment of the present disclosure, the flow of fluid can be enhanced by forming the interior surface of capillary tube 110 from a material which is hydrophilic. In another embodiment of the present disclosure, the flow of fluid can be enhanced by forming the interior surface of capillary tube 110 from a material which has been treated to be hydrophilic. In yet another embodiment of the present disclosure, the flow of fluid can be enhanced by forming the interior surface of capillary tube 110 from a material which has been coated with a hydrophilic material such as a surfactant or hydrophilic polymers. Exemplary methods of treating interior surfaces of capillary tube 110 include treating using polyamides and oxidation (e.g. corona/plasma treatment); plasma chemical vapor deposition; vacuum vapor deposition of metals, metal oxides or non-metal oxides; deposition of an element which oxidizes with water; and the like. The interior channel of the capillary tube 110 can also be coated with an anti-coagulant material in order to facilitate blood flow into the device. The capillary tube can include a cap or alternative method to close access to air and moisture once the sampling is completed.

Figure 1C:
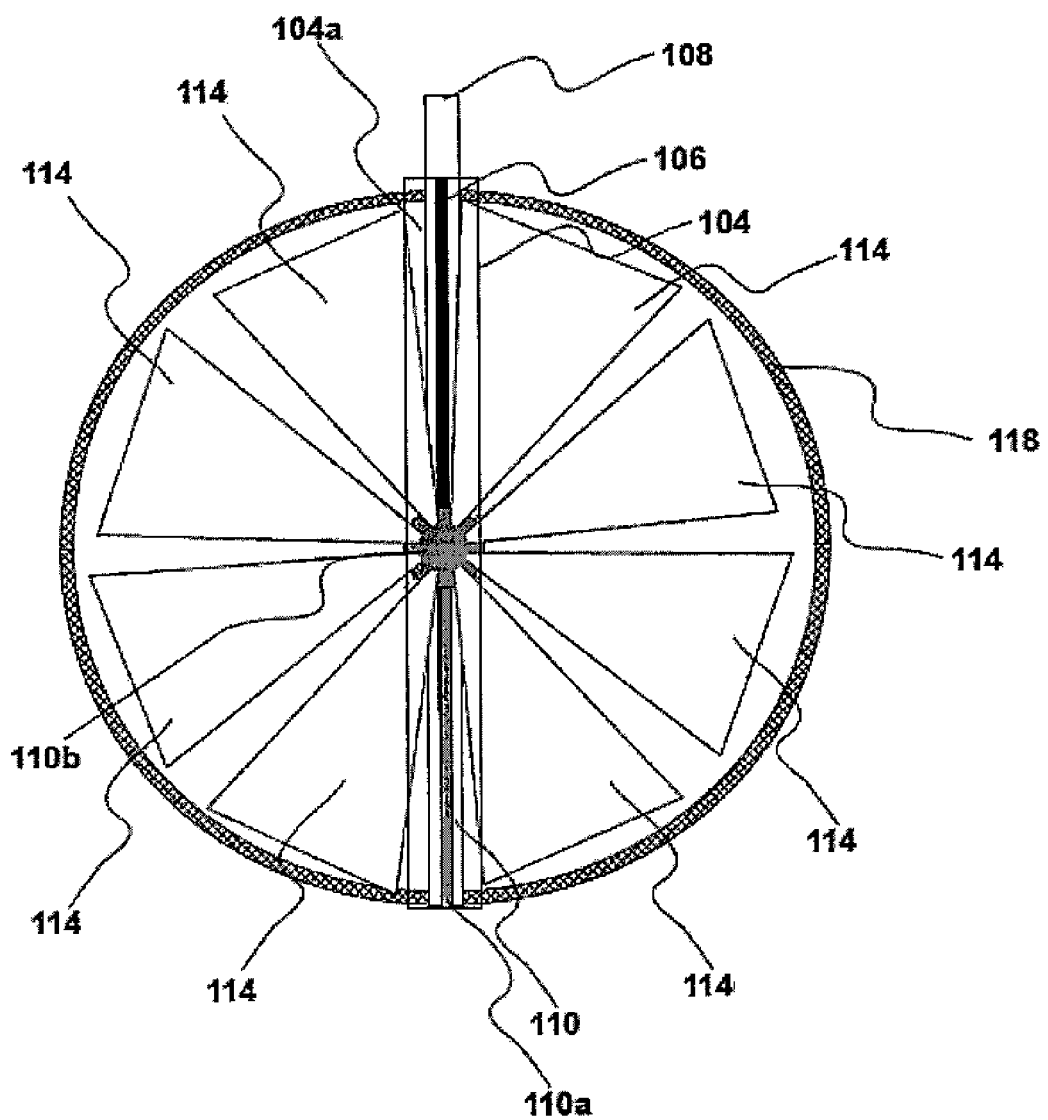
FIG. 1C illustrates a bottom sectional view of an embodiment of the apparatus of the present disclosure.

Distal end of capillary tube 110 includes a reservoir 110b, as shown in FIG. 1C, to collect body fluid drawn through capillary space 110a. In one embodiment of the present disclosure, an absorbent pad can be placed in capillary space 110a for wicking body fluid through capillary space 110a to reservoir 110b. Exemplary absorbents that can be used for wicking body fluids include paper, cloth, gel, powder or polymer materials and the like.

Figure 1D:
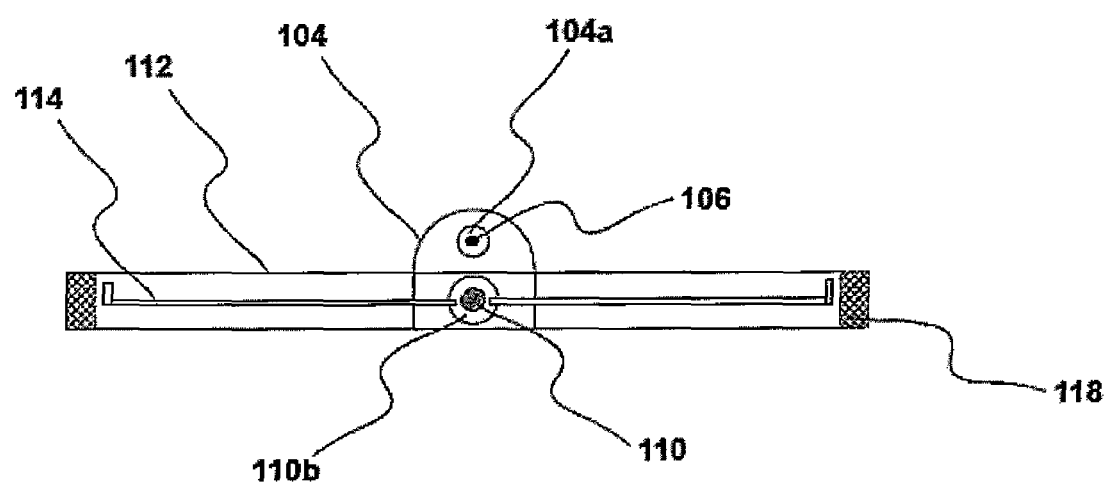
FIG. 1D illustrates a side sectional view of an embodiment of the apparatus of the present disclosure.

Referring now to FIGS. 1C and 1D there is shown a bottom cross-sectional view of apparatus 100 taken about line II-II of FIG. 1A, and side cross-sectional view of apparatus 100 taken about line III-III of FIG. 1A. Main body 102 of apparatus 100 further includes a sample compartment 112 for holding sampling and storage materials 114. Sample compartment 112 within main body 102 allows collection materials 114 to be placed into apparatus 100 and received within reservoir 110b such that the collection material 114 is disposed radially around reservoir 110b and adjacent to lancet 106. Collection materials 114 can be pre-cut, partially cut or perforated in order to more easily separate individual samples for testing. Alternatively the collection material(s) can be a different shape such as squares, rectangles, oval or circles. In certain embodiments, the collection material is provided as pre-cut wedges as shown in FIGS. 1B and 1C. Embodiments of the invention may also include a sample sup port structure, which can be flat with an even surface thickness or it can have varying surfaces such as raised channels or ridges to aid fluid flow. The sample support may also have holes or slots to aid in fluid or gas transfer. This support may be an integral part of the top or bottom structural components, or it may be a separate removable component. The collection material 114 contacts the fluid when capillary action of the capillary tube 104 draws the body fluid into reservoir 110b. Upon contacting collection material 114, fluid from reservoir 110b is absorbed into collection material 114. In certain embodiments of the present disclosure, an apparatus 100 can contain two or more pieces of collection material 114 so long as all pieces are in fluid contact with the reservoir.

The collection material 114 can be any suitable material capable of absorbing body fluids. Exemplary materials that can be used to manufacture the collection material 114 include filter paper or other solid support made from materials including nylon, polypropylene, polyester, rayon, cellulose, cellulose acetate, mixed cellulose ester, glass microfiber filters, cotton, quartz microfiber, polytetrafluoroethylene, polyvinylidene fluoride and the like. In preferred embodiments of the disclosure, the collection material is in a form comprising one or more sheets of such collection material, with a shape comprising a small central disk from which radiate a number of identical protrusions (or "petals") separated by a number of empty spaces (which may be imagined similar to a daisy with petals) such that a sample is contacted with the central disk and is absorbed into the protrusions. The size of the sample collection material, the central disk, and the size and number of protrusions may be easily determined by one skilled in the art based on 1) the amount of sample needed, 2) the type of fluid collected, 3) the number of tests to be conducted, and 4) the preservative properties of the sampling material (below), amongst other factors. The empty spaces between the protrusions allow for increased drying speed and contact with a support structure for stability. The protrusions are so designed as to be easily separable from the central disk, so that each petal may be detached and tested-since each petal has a uniform area and thickness, the amount of sample absorbed on each should be identical. The shape of the protrusions may be of any shape suitable for easy connection or detachment from the central disk, such as wedges, triangles, rectangles, ovals, or the like. In some embodiments, the petals may be of differing sizes, each size designed to collect a certain specific volume of sample. In some embodiments of the presenting disclosure, collection material 114 can be chemically treated to inactivate bacteria and/or viruses; to denature proteins; to lyse cells, to inactivate proteases, RNAses, DNAses and other enzymes, and/or to aid in sample preparation. In other embodiments of the present disclosure, different areas of the collection material 114 or different pieces if more than one, can be treated with different chemicals for use to inactivate bacteria and/or viruses; to denature proteins; and/or to aid in sample preparation and/or other uses described above. Additionally, the composition of the collection material 114 in a single apparatus can differ to allow for improved sample analysis for different analytes; for instance, a portion can be material optimized for DNA assays, a second portion can be optimized for small molecule analysis and a third portion can be more suitable for protein assays. The collection material 114 can be of any color, and in certain embodiments is a light color such as white, off-white or tan such that the progress of the blood and completion of the sample filling can be observed. Exemplary chemicals used for treating collection material 114 include detergents, pH-altering chemicals, chelators, denaturing agents such as urea, enzymatic inhibitors, and the like.

The following table illustrates data confirming even sample distribution with consistent weight of dried blood plus collection material for each of 8 petals in the fan configuration. Whole human blood (70 μL) was applied to the center section of the fan, dried in the presence of desiccant and each petal was then plucked and weighed. Low percent relative standard deviations (RSD) of between the final petal weights demonstrate consistent sample distribution:

| Petal with dried blood | Weight (mg) | | | |
| --- | --- | --- | --- | --- |
| | Ahlstrom 226 | Ahlstrom 205 | Whatman CF10 | Whatman CF12 |
| 1 | 4.8 | 5.1 | 4.8 | 5.4 |
| 2 | 5.3 | 5.2 | 4.9 | 5.2 |
| 3 | 5.3 | 5.0 | 5.0 | 5.4 |
| 4 | 4.8 | 5.1 | 4.8 | 5.2 |
| 5 | 5.2 | 5.3 | 4.7 | 5.0 |
| 6 | 5.1 | 5.0 | 4.8 | 5.0 |
| 7 | 5.3 | 5.2 | 4.8 | 5.3 |
| 8 | 5.1 | 5.3 | 4.8 | 5.0 |
| Average | 5.1 | 5.2 | 4.8 | 5.2 |
| Std Dev | 0.2 | 0.1 | 0.1 | 0.2 |
| RSD % | 4.1 | 2.3 | 1.8 | 3.3 |

Certain commercially available absorbent materials can also be included in the disclosed devices. Materials are available for use in various types of testing, drug metabolism, toxicology, viral detection, protein or genetic analysis, etc. For certain embodiments, devices can contain a solid matrix such as a Whatman FTA® DMTK, Whatman 903™ Specimen Collection material (Whatman, Inc. Piscataway, N.J.), Ahlstrom 226 paper, or other absorbent material deemed suitable for biofluid collection.

The sample compartment can further include a drying agent 118 to remove moisture from body fluid absorbed on the collection material and to facilitate storage of the absorbed body fluid in the device for extended periods of time. In one embodiment of the present disclosure, drying agent or desiccant 118 can be placed within the storage compartment along the circumference of the main body 102, as shown in FIGS. 1B-D. In another embodiment of the present disclosure, drying agent 118 can be placed along all sides of each sample section. In some embodiments, a thin film separates the drying agent from the absorbent material such that the film can be removed following fluid collection to allow access to the drying agent. In yet another embodiment of the present disclosure, drying agent 118 can be placed above and below the collection material. Exemplary drying agents used to remove moisture from biological fluid absorbed on the collection material can include any of the following: silica gel, aluminum oxide, calcium sulfate, magnesium sulfate, molecular sieves, and the like.

Main body 102 and the internal compartments can be made from any suitable material, and typically can be economically produced from plastics, glass, or various other materials, for example by injection molding or extrusion. In one embodiment of the present disclosure, main body 102 and collection compartment 112 are manufactured of a transparent material such as glass, plastic, polyvinyl chloride or any similar biocompatible plastic. In another embodiment of the present disclosure, main body 102 and collection compartment 112 are manufactured having an opaque or solid appearing surface. In some embodiments it is desirable to have the capillary transparent, or to include a window portion to allow the user to observe the progress of fluid filling the capillary tube and/or to facilitate viewing the sampling of the body fluid, particularly by optical means.

Lancet 106 can be composed of any bio-compatible material such as steel, surgical stainless steel, aluminum, or titanium, as well as many other suitable materials known in the art. Preferably lancet 106 is made in a solid piece which is sufficiently sharpened to create an incision. Lancet mechanisms for finger prick or similar blood collection uses are known in the art (such as that of the patent application of Karbowniczek, Ser. No. 11/123,849) and can be spring loaded so that depressing a trigger or button releases the lancet and drives it into the tissue to produce a small blood flow. Importantly, any of such appropriate lancet devices known or used in the art can be adapted for use in the disclosed fluid collection devices.

Sterility of the unit can be maintained by sealing proximal end 110c of lancet hub 104 to enclose lancet 106 and sealing capillary tube 110 to prevent contamination of sampled and stored body fluid. In one embodiment, a cap is maintained over proximal end 110c of lancet hub 104 to enclose lancet 106 and seal capillary tube 110. The cap can be removed prior to use and replaced after use. In another embodiment of the present disclosure, a membrane is positioned over proximal end 110c of lancet hub 104 to enclose lancet 106 and seal capillary tube 110. The membrane is composed of a suitable material through which the lancet can extend during use. Exemplary membrane materials include rubber, silicone, plastics and the like. In one exemplary use of the present disclosure, the proximal end 110c of lancet hub 104 of apparatus 100 is placed over an appropriate incision site, such as a fingertip, such that the proximal end abuts the skin surface. In the refracted position, the proximal tip 106a of lancet 106 is fully received within the lancet hub 104, preventing accidental contact with the tip. A downward force is then applied to lancet trigger 108, displacing lancet 106 from a retracted position to an extended position. In the extended position, proximal tip 106a of lancet 106 penetrates the skin tissue thereby creating a small incision, typically 0.8 to 2.5 mm deep. The incision depth will typically be pre-set at a desired level, or can be controlled by a selectable depth adjustment mechanism included on the unit.

Figure 2:
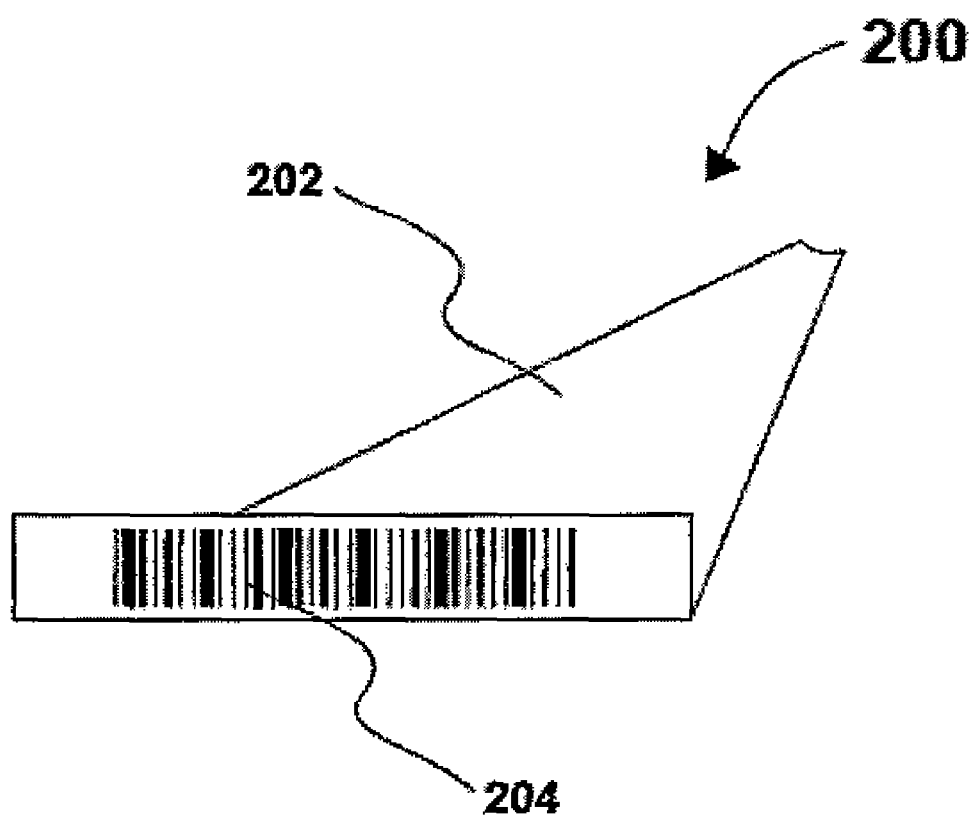
FIG. 2 illustrates an exemplary bar code for use with this invention.

The downward force applied to lancet trigger 108 is then released causing lancet 106 to move into the retracted and protected position. After retraction, apparatus 100 remains over the newly formed incision, preferably without movement, and body fluid is drawn into capillary tube 110 by capillary action. A sufficient volume of body fluid is drawn into capillary space 110a and collected in reservoir 110b. Collection material 114 radially located in reservoir 110b contact the body fluid and absorbs the biological fluid. Absorbed body fluid on collection material 114 is dried by removal of moisture by drying agent placed in sample compartment 112. Collection materials 114 can individually be tagged by unique identifiers. In one embodiment of the present disclosure, collection material 114 can be tagged by barcodes, as shown in FIG. 2. Apparatus 100 can also be tagged by unique identifiers. In one embodiment of the present disclosure, apparatus 100 can be tagged by barcode. In another embodiment of the present disclosure, apparatus 100 can be tagged by radio frequency identification (RFID) tags. Associated information might include subject identification, sample number, sample conditions such as time and date and any other relevant data Thus, the body fluid can be sampled and stored for extended periods of time.

In some embodiments of the present disclosure, apparatus 100 can also include means for analyzing biological fluid sampled and stored on an absorbent collection material contained in the storage compartment using apparatus 100. Exemplary biological fluids that can be sampled and stored using apparatus 100 include whole blood, plasma, serum, urine, saliva, cerebrospinal fluid, tissue culture supernatants, bronchoalveolar lavage, synovial fluid, tissue extracts, tears, skin washings, etc.

Figure 3:
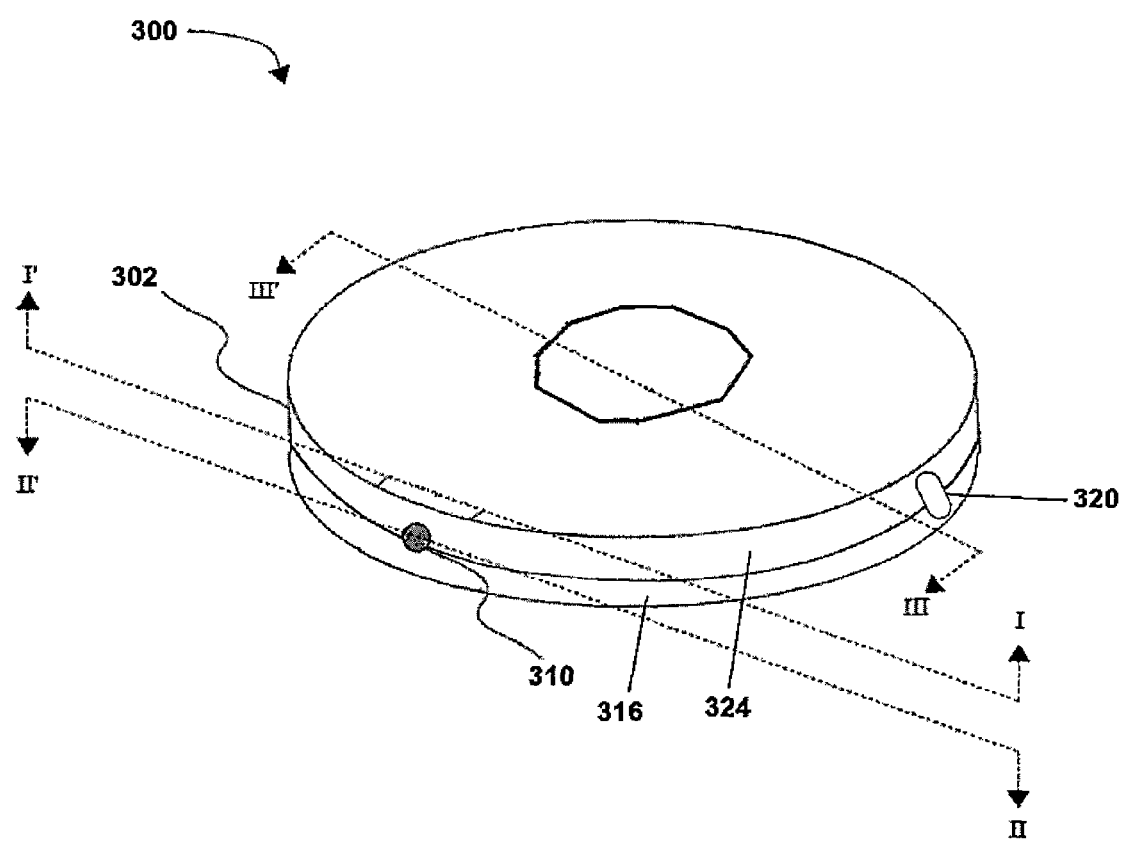
FIG. 3 illustrates an embodiment of a collection and storage device that does not include a lancet.

In certain embodiments of the disclosure, no lancet is included in the device because penetration of tissue is not required to obtain a liquid sample. Examples of such fluids include, but are not limited to separated blood products such as plasma or serum, urine, saliva, cerebrospinal fluid, a tissue culture supernatant, bronchoalveolar lavage, synovial fluid, a tissue extract, tear, a skin washing, or any other fluid that is already accessible without piercing the skin. An example of such a device 300 is shown in FIG. 3. This device includes a body 302 with a top 324 and bottom 316 movable by a hinge 322 to open or close, however, other means of reversibly connecting the top and bottom are envisioned, such as, for example, screwing the top and bottom together, or sealing them together with fiction. As in the lancet containing devices, device 300 includes a capillary tube 310, a reservoir 310b with absorbent material to communicate a fluid to a solid support material within an inner compartment.

In other embodiments of the invention, the lancet and its delivery mechanism as described above may be housed in a separate, detachable component, so that the lancet delivery mechanism may be detached after use or when not needed (See FIG. 6 below).

Collection material 114 with absorbed and dried body fluid can be removed from the collection chamber 112 and analyzed using standard chemical, optical or electro-chemical methods. Exemplary analytical techniques include standard methods for diagnostic testing including liquid chromatography, mass spectrometry (LC-MS/MS), immunochemistry, fluorescence, ultraviolet and/or visible spectrometry (UV-VIS), luminescence, reactive dye, microarray, RT-PCR, DNA and RNA sequencing and hybridization methods.

In certain embodiments of the disclosure, the sample can be measured directly from the device. For example, a color change or other visual indicator can be detected upon sample exposure to a chemical or reagent laced into the absorbent collection material. Such visual tests are known in the art and include, but are not limited to detecting the presence of an enzyme reaction, a binding reaction, or a change in pH, for example.

Figure 4:
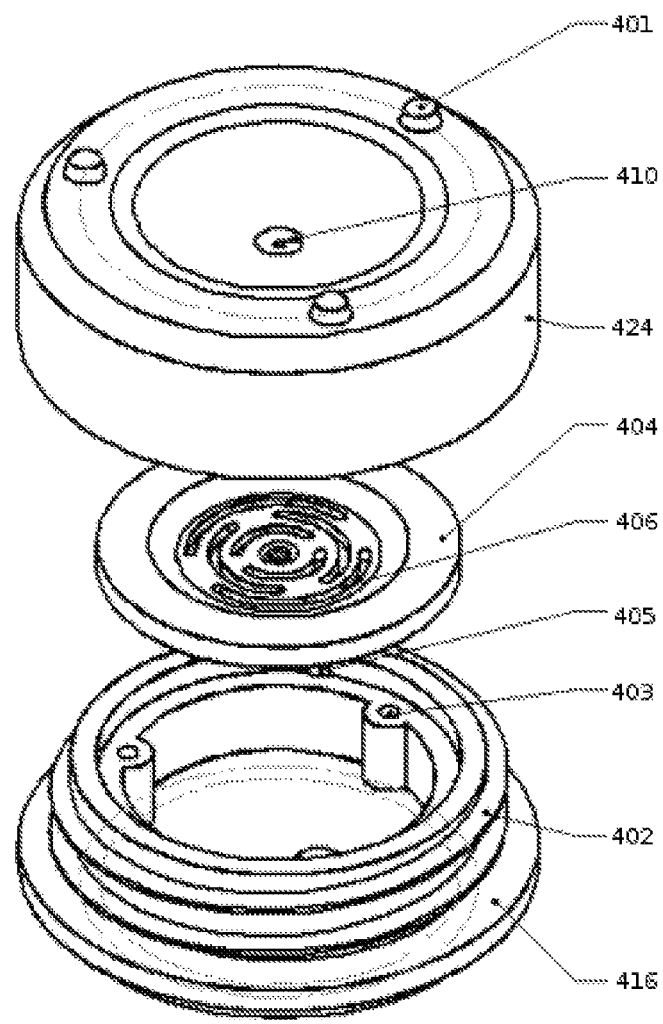
FIG. 4 is an exploded diagram of a screw-together embodiment of the invention.

Turning to FIG. 4, there is shown an exploded diagram of an example screw-together, lancet-less embodiment of the present invention, shown so that one may understand how the discussed components are arranged within the device; the components and their various modifications and embodiments are described more fully above. Stacking pegs or recesses 401 on the top half portion 424 that fit together with corresponding stacking holes or pegs (not shown) on the bottom portion 416 of the device are present to make multiple units stable when stacked. Other mechanism besides pegs/holes, such as slots, dovetails, screws, amongst others may be used to provide for a stacking mechanism. The top portion 424 also contains a capillary tube 410 for transferring fluid from the outside to the inside of the device, and is in fluid communication with the sampling material (not shown). The bottom 416 and top 410 portions screw together via threading 402 as discussed above, other mechanisms suitable for joining portions other than screwing may be used. On the bottom or top portions as desired may be found slots, holes, or other reversible connection mechanisms 403 suitable for attaching the filter paper/collection material support component 404 (filter paper/collection material not shown), on which may be located tabs, slots, or other connectors for fitting with and securing to the connection mechanism of 403. Note that in this embodiment, after the sample collection material support 404 attaches to the bottom component 416, there is formed a chamber of substantial volume between the two that may be used to house a desiccant material as described above. The filter paper support 404 may also contain slots or holes for moisture or gas transfer 406 to the open chamber below.

Figure 5:
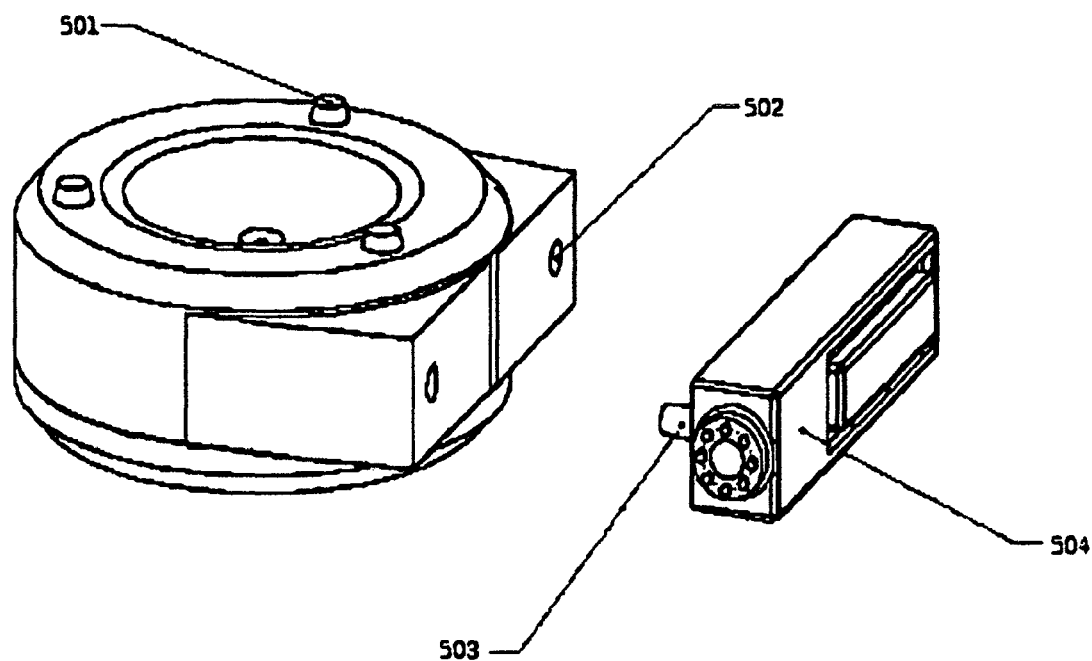
FIG. 5 is view of an embodiment of the invention with a detachable lancet mechanism.

Turning to FIG. 5, there is shown an embodiment of the present invention with a detachable lancet mechanism, as discussed above. The main body of the unit 501 has one or more attachment mechanisms 502 such as recesses, pegs, slots, holes, screws, or dovetails (pegs are used in this figure), amongst others that fit together with corresponding attachment mechanisms 503 located on the detachable lancet delivery component 504.

Figure 6:
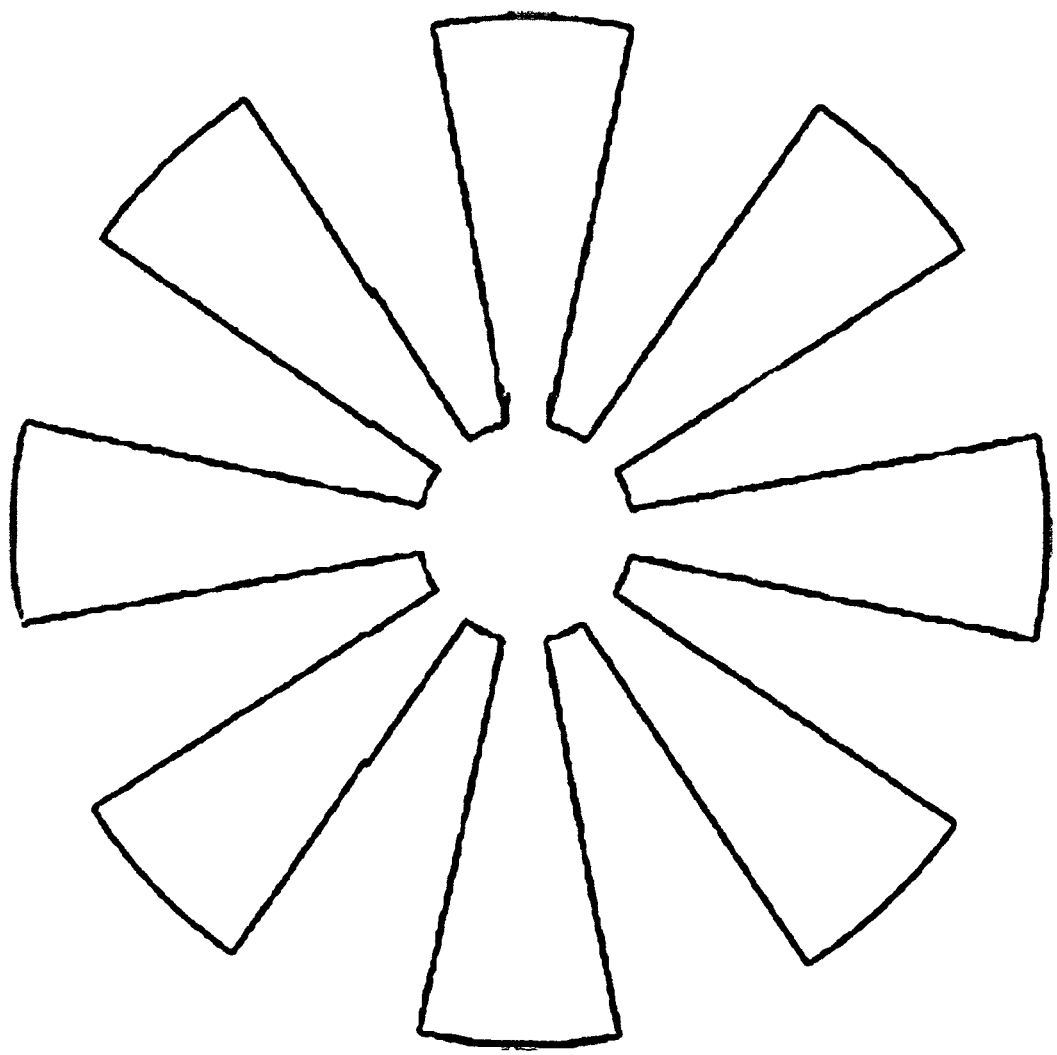
FIG. 6 is a view of a special configuration of sampling material suitable for use with the invention.

Turning to FIG. 6, there is shown an exemplary embodiment of the modified form of collection materials envisioned within the present invention. The "petaled" shape, compared to a traditional circle shape, allows for: 1) consistent sample distribution between the petals 2) improved ability to remove small samples from the whole, 3) rapid drying rate, and 4) improved stability of the collection material, as the collection material support structure described above may be made with slots or protrusions that correspond to the "petaled" shape, allowing the collection material support structure to "grasp" the collection material and prevent it from moving around within the device.

Figure 7:
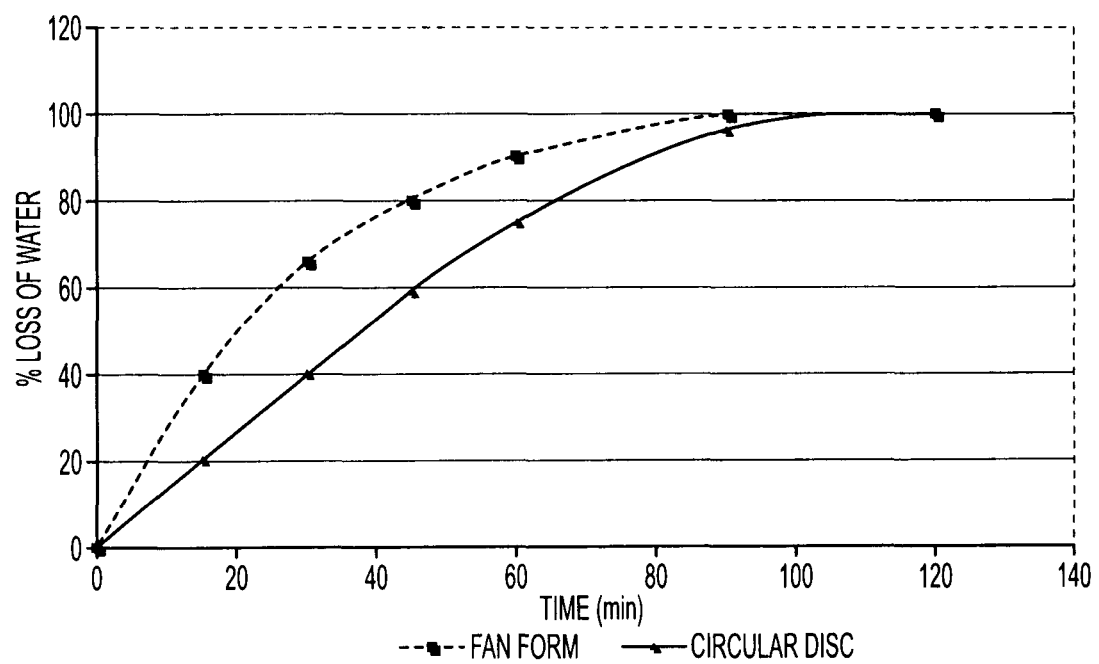
FIG. 7 provides a graph that illustrates data confirming increased drying rate of the fan form disc as compared to the traditional circular disc.

The graph at FIG. 7 illustrates data confirming increased drying rate of the fan form as compared to the traditional circular disc. Whole human blood (70 μL) was applied to the center section of the fan or circular disc form of 903 filter paper, dried in the presence of desiccant and weighed to determine loss of water at the indicated time points. At 15 minutes, the rate of drying is approximately 2× faster for the fan form, and is substantially died (80% water loss) 40 minutes earlier. It is important to note that in addition to faster drying, a desic-cant will ensure that any additional moisture that may make its way into the sample (as by exposure to environmental moisture) is readily removed.

The one-step body fluid sampling and storage apparatus of the present disclosure and many of its attendant advantages will be understood from the foregoing description and it will be apparent that various changes can be made in the form, construction, or arrangement of parts thereof without departing from the spirit and scope of the disclosure or sacrificing all of its material advantages, the forms described being merely preferred or exemplary embodiments thereof.

We claim:

1. A sampling and storage device for biological fluids comprising:
   a body comprising:
      two or more structural components that can at least partially be attached and detached from one another and can form an open and a closed configuration, having a top portion and a bottom portion in the closed configuration, wherein the components form one or more interior cavities when in the closed configuration;
      a carrier that is disposed on the top surface of the top portion, wherein the carrier extends from one edge of the body to the opposing edge and comprises a channel;
      a capillary tube contained in the channel of the carrier and extending from an exterior of the device to a fluid reservoir and in fluid communication with the one or more interior cavities;
      one or more collection compartments formed in the one or more interior cavities and in fluid communication with the capillary tube;
      one or more pieces of sampling material placed within the one or more collection compartments and in fluid communication with the capillary tube; and
      a desiccant contained within the cavities in vaporous communication with the sampling material, and suitable for drying a collected sample and maintaining low humidity in the device; and
   a mechanism for sealing the device from the environment after use.

2. The device of claim 1, wherein the sampling material is a solid support comprising nylon, polypropylene, polyester, rayon, cellulose, cellulose acetate, mixed cellulose ester, glass microfiber filter, cotton, quartz microfiber, polytetrafluoroethylene, polyvinylidene fluoride, filter paper or a combination of any thereof, or one or more sheets of absorbent material.

3. The device of claim 1, wherein the sampling material, the capillary tube or both comprise an anticoagulant.

4. The device of claim 1, wherein the sampling material comprises a detergent, a chelator, a pH modulating chemical, an enzyme inhibitor, a denaturant, or a combination thereof.

5. The device of claim 1, wherein the biological fluid is whole blood, plasma, serum, urine, saliva, cerebrospinal fluid, a tissue culture supernatant, bronchoalveolar lavage, synovial fluid, a tissue extract, tear, or a skin washing.

6. The device of claim 1, further comprising one or more identification mechanisms.

7. The device of claim 6, wherein the identification mechanism is one or more bar code tags, one or more RFID tags or a combination thereof affixed to the device.

8. The device of claim 1, further comprising one or more identification mechanisms attached to the sampling material.

9. The device of claim 8, wherein the identification mechanisms are one or more barcode tags, RFID tags, or a combination thereof.

10. The device of claim 1 wherein the sealing mechanism is selected from a sticker placed over the outside opening of the capillary tube, a plug placed within the capillary tube, a movable door or slide that can be positioned to cover the capillary opening, pinching or twisting the capillary tube so that it is sealed, and replacing the capillary tube containing structural component with a structural component not containing a capillary tube.

11. The device of claim 1 further comprising a lancet device within the channel of the carrier that is effective to cause a small wound in the subject to create a blood flow for collection in the device.

12. The device of claim 1 wherein the sampling material comprises a central disk from which radiates a plurality of protrusions, wherein each protrusion contacts only the central disk and does not contact any other protrusion, and wherein the plurality of protrusions and central disk substantially define a fan-shape.

13. A method of sampling and storing a biological fluid from a subject for testing comprising:
- contacting a biological fluid of the subject with the end of the capillary tube of the device of claim 1 effective to draw the biological fluid into the one or more interior cavities and into contact with the sampling material;
- drying the biological fluid absorbed into the sampling material; and
- storing the dried biological material in the device.

14. The method of claim 13, further comprising shipping the device containing the dried biological sample to a location remote from the collection site for testing.

15. The method of claim 13 wherein the sampling material is removed from the device for testing.

16. The method of claim 13, wherein at least a portion of the sampling material comprises a chemical test reagent that reacts to a characteristic or component of a biological fluid.

17. The method of claim 16 wherein the reaction results in a color change.

* * * * *

UNITED STATES PATENT AND TRADEMARK OFFICE
CERTIFICATE OF CORRECTION

PATENT NO.         : 9,040,236 B2
APPLICATION NO.    : 13/817442
DATED              : May 26, 2015
INVENTOR(S)        : Jeanette Hill et al.

It is certified that error appears in the above-identified patent and that said Letters Patent is hereby corrected as shown below:

Specification

Column 1, after Title of the Invention

Insert -- STATEMENT REGARDING FEDERALLY SPONSORED RESEARCH OR DEVELOPMENT
This invention was made with government support under W31P4Q-11-C-0234 awarded by Defense Advanced Research Projects Agency (DARPA). The government has certain rights in the invention. --

Signed and Sealed this
Seventeenth Day of November, 2015

Michelle K. Lee
*Director of the United States Patent and Trademark Office*